United States Patent [19]

Leach

[11] 4,125,736

[45] Nov. 14, 1978

[54] METHOD FOR THE DISPROPORTIONATION OF HIGHLY ALKYLATED PHENOLS WITH PHENOL

[75] Inventor: Bruce E. Leach, Ponca City, Okla.

[73] Assignee: Continental Oil Company, Ponca City, Okla.

[21] Appl. No.: 852,389

[22] Filed: Nov. 17, 1977

Related U.S. Application Data

[62] Division of Ser. No. 762,083, Jan. 24, 1977.

[51] Int. Cl.$^2$ ............................................. C07C 37/16
[52] U.S. Cl. ................................................. 568/804
[58] Field of Search ............ 260/621 R, 621 E, 621 D, 260/624 C

[56] References Cited

U.S. PATENT DOCUMENTS

| | | | |
|---|---|---|---|
| 3,968,172 | 7/1976 | Ichikawa et al. | 260/621 R |
| 4,060,560 | 11/1977 | Leach | 260/621 E |

*Primary Examiner*—James O. Thomas, Jr.
*Assistant Examiner*—Warren B. Lone
*Attorney, Agent, or Firm*—Cortlan R. Schupbach, Jr.

[57] ABSTRACT

This invention provides an improved process for the disproportionation of highly alkylated phenols with phenol using an improved magnesium oxide catalyst promoted with tungsten oxide, silica sol, and sodium silicate. The method provides a catalyst having a high reactivity, high surface area, and high crush strength compared to known magnesium oxide, tungsten oxide catalysts. The catalyst is useful in phenol methylation and disproportionation. The effect of silica sol and sodium silicate is synergistic since these materials alone will not catalyze these reactions. Surprisingly, the catalyst will not disproportionate olefins.

6 Claims, No Drawings

METHOD FOR THE DISPROPORTIONATION OF HIGHLY ALKYLATED PHENOLS WITH PHENOL

This application is a divisional of Ser. No. 762,083 filed Jan. 24, 1977.

This invention comprises an improved catalyst and method for the disproportionation of highly alkylated phenols with phenol to form cresols and xylenols. More specifically, this invention comprises a process utilizing an improved tungsten oxide promoted magnesium oxide catalyst which has in addition, sodium silicate and silica sol in useful amounts. The effect is synergistic since silica sol and sodium silicate alone will not catalyze the reactions of the instant invention.

Meta-para cresols have been previously synthesized by methylation of phenol using high acidity catalysts such as aluminas or silicas, phosphoric acid on Kieselguhr, and the like. Other patents teach processes such as proportionation reaction using alumina catalysts with or without silicas as taught in U.S. Pat. No. 3,417,149. British Pat. No. 1,291,191 teaches liquid phase disproportionation in the presence of catalysts such as aluminum phenolate, metholate, or oxide. Vapor phase methylation of phenols over magnesium oxide is taught in U.S. Pat. No. 3,479,410, which also requires the presence of 2,4,6-trimethylphenol as an ingredient in the feedstream. The invention is useful for phenols having at least one orthohydrogen. Catalysts containing magnesium oxide and tungsten oxide are known for the disproportionation of olefins. Examples of such processes can be found in U.S. Pat. No. 3,491,163, which teaches production of long-chain linear olefins by contacting catalysts such as magnesium oxide together with tungsten oxide and silica and U.S. Pat. No. 3,760,026 which teaches the use of a catalyst comprising magnesium oxide and tungsten oxide together. U.S. Pat. No. 3,786,112 teaches the use of an olefin disproportionation catalyst comprising tungsten oxide on silica together with magnesium oxide, each component being pretreated with potassium hydroxide. Japanese publication No. 69 27,367 teaches phenol methylation over magnesium oxide catalysts in the presence of an elemental metal such as copper, zinc, molybdenum, tungsten, platinum and palladium.

These catalysts, while useful for various reactions, have not hitherto been sufficiently reactive for many reactions involving conversion of alkylated phenols. In particular, these catalysts have lacked the high reactivity, surface area and crush strength necessary for the conditions of such alkylations. It would therefore be of great benefit to provide an improved catalyst and process for the disproportionation of alkylated phenols.

It is therefore an object of the present invention to provide an improved catalyst for the disproportionation of alkylated phenols, xylenols or cresols, the catalyst being selective to this end. Other objects will become apparent to those skilled in this art as the description proceeds.

It has now been discovered in accordance with the present invention that a catalyst sufficiently active for the disproportionation of phenols with higher methylated phenols in the presence of 1-10 weight percent water is comprised of magnesium oxide, 2-5 weight percent tungsten oxide added as tungstic acid ($H_2WO_4$), 1-5% sodium silicate ($na_2SiO_3$), 1-5 weight percent silica sol ($SiO_2 \times H_2O$) and preferably, although not critically, 1-2 weight percent of graphite binder, all weights being calculated upon the weight of the total catalyst. It is necessary that water be present in the feed when using this catalyst for disproportionation. Water content can range from about 1 to about 15 weight percent, based on the total feed, but from about 5 to about 10 weight percent is the most preferred range.

The cresols and xylenols of the instant invention are useful as modifiers for phenol formaldehyde resins, as chemical intermediates to phenol derivatives, the synthesis of Vitamin E and in polymerization processes. For example, 3,5-xylenol is useful for these purposes and is normally derived as a minor component from phenol methylation. An alternate route is the production from acetone in the presence of water over a magnesium oxide catalyst as described in U.S. Pat. Nos. 3,803,249, 3,816,546, and 3,827,947.

The catalyst of the present invention is prepared using the following procedure. One hundred lbs. of catalyst will normally be comprised of 89 lbs. of magnesium oxide, 3 lbs. of tungstic acid, preferably as a dry powder suitable for dry blending with magnesium oxide, 3 lbs. of silica sol, and 3 lbs. of sodium silicate. Two lbs. of graphite will normally be added as a dry lubricant should catalyst tableting be desired. However, the graphite adds little or nothing to the effectiveness of the catalyst. Preferred magnesium oxides are those having a high surface area such as Merck Maglite D. For example, this catalyst when calcined at 450° C has a surface area of about 200 square meters per gram whereas many other magnesium oxide catalysts have surface area below 50 square meters per gram.

The preparation procedure is as follows; the magnesium oxide, tungstic acid and optional graphite are mixed. Sodium silicate and silica sol are added in aqueous solutions using 0.5 to 1.0 lbs. of water per lb. of magnesium oxide. The material is usually pelletized and calcined at 450° C for between 1 and 2 hours.

A catalyst prepared as described above will have a density of between 50 and 55 lbs. per cubic foot, 120-175 square meter per gram surface area, an average pore volume of 0.40 cubic centimeters per gram, and an average pore size of about 120 angstroms. Calcined crush strength is around 20 lbs. or about 25 lbs. uncalcined.

The catalyst herein is superior in crush strength, surface area, and conversion to catalysts not containing silica sol and sodium silicate, including catalysts containing only one of the two additives as described in the references set forth above.

The invention is more concretely described with reference to the examples below wherein all parts and percentages are by weight unless otherwise specified. The examples are designed to illustrate the present invention and are not to be construed to limit it.

The reactor used in the examples generated herein was an electrically heated 1-inch diameter pipe having a 200 cubic centimeter volume. The reaction occurred at the hottest part of the bed not carboned. Unless otherwise stated, catslyst samples were calcined at about 45° C for about 2 hours to develop surface area.

EXAMPLE 1

The catalyst was evaluated using distilled phenol and 2,6-xylenol feeds. The reaction was initiated at 460° C and increased to 475° C gradually over a 90 hour period during which the reaction took place. The product contained over 25 weight percent ortho-cresol throughout the run. Similar results had been obtained with a known catalyst containing only tungsten oxide. Carbon content on the catalyst of the instant invention after 90 hours was 5.25%. Surface area after regeneration was 90 square meters per gram. Catalyst deactivation occurred in other runs when the carbon content was 12%. Composition of the feed and product samples are given in Table 1.

Table 1

| WO₃/MgO CATALYST with 3% NaSiO₃, 3% Silica Sol | | | | | | | | |
|---|---|---|---|---|---|---|---|---|
| Hrs on Steam | | 2 | 6 | 24 | 48 | 72 | 96 | 6* |
| Temperature, °C | | 460 | 460 | 460 | 460 | 465 | 465 | 460 |
| Composition w/o | Feed | | | | | | | |
| Water | 9.1 | | | | | | | |
| Phenol | 43.0 | 37.9 | 34.0 | 32.9 | 32.7 | 32.4 | 33.4 | 31.4 |
| o-Cresol | 0.6 | 17.0 | 23.1 | 25.0 | 24.2 | 24.8 | 22.8 | 27.5 |
| m,p-Cresol | 5.1 | 5.7 | 7.0 | 6.7 | 5.7 | 5.4 | 5.0 | 6.4 |
| 2,6-Xylenol | 51.3 | 33.2 | 26.7 | 27.4 | 30.8 | 31.4 | 34.3 | 25.7 |
| 2,4/2,5-Xylenol | | 2.9 | 5.7 | 5.4 | 4.4 | 4.1 | 2.9 | 6.1 |
| 2,3-Xylenol | | Tr | 0.1 | Tr | 0.1 | Tr | Tr | Tr |
| 2,4,6-Trimethylphenol | | 3.3 | 3.4 | 2.6 | 2.2 | 1.9 | 1.6 | 2.9 |

*After regeneration

In order to compare the present catalyst with one of the prior art, a catalyst comprising magnesium oxide (Merck Maglite D, 1/8" diameter pellets) and 3 weight percent $H_2WO_4$ (prior catalyst) was used to disproportionate a feed mixture consisting of, by weight, 40 parts phenol, 54 parts 2,6-xylenol, 6 parts mixed cresols and 10 parts $H_2O$. The reaction was carried out continuously at a liquid hourly spaced velocity (LHSV) of 1.0 and at temperatures of 450° and 460° C. Weight percent of reaction products for each temperature were:

|  | 450° C | 460° C |
|---|---|---|
| Phenol | 30.8 | 28.2 |
| o-cresol | 25.1 | 30.0 |
| 2,6-xylenol | 25.3 | 18.0 |

Catalyst pellets made using the catalyst in the instant invention are stronger uncalcined (27 lb crush strength) than calcined (19 lb crush strength). It is therefore preferred to transport and load catalysts in an uncalcined state. The catalyst can then be calcined in place at about 450° C for about 2 hours to develop the surface area. If the reaction is begun without calcining, the surface area of the magnesium catalyst is about 70 square meters per gram and the catalyst only slowly gains activity and does not reach the level of activity of calcined samples. In addition the temperature must be increased to maintain even a lower level of activity at much slower cycle times than observed for the same calcined sample as shown in Table 1. Even after regeneration the high level of activity typically observed does not return, indicating that permanent damage to the uncalcined catalyst has resulted. Regeneration is accomplished in the same fashion known for magnesium oxide catalysts alone. The presence of silica sol and sodium silicate in the catalyst improves crush strength and stabilizes the magnesium oxide in a high surface area state. Sodium silicate level determines crush strength and the catalysts containing colodial silica have higher surface areas and are more active. Table 2 shows the performance of an uncalcined catalyst, and is comparable to Table 1 results.

Table 2

| Uncalcined catalyst | | | | | | | | |
|---|---|---|---|---|---|---|---|---|
| Hrs on steam | | 2 | 6 | 26 | 48 | 72 | 96 | 6* |
| Temperature, °C | | 460 | 460 | 460 | 465 | 480 | 490 | 460 |
| Composition w/o | Feed | | | | | | | |
| Water | 9.09 | | | | | | | |
| Phenol | | 38.3 | 34.5 | 33.4 | 33.8 | 32.7 | 36.0 | 35.7 |
| o-Cresol | | 12.4 | 20.4 | 22.8 | 19.4 | 22.2 | 21.2 | 20.9 |
| m,p-Cresol | | 5.2 | 6.3 | 5.5 | 5.2 | 5.4 | 4.5 | 6.3 |
| 2,6-Xylenol | | 39.8 | 31.2 | 32.1 | 37.8 | 35.1 | 35.1 | 29.5 |
| 2,4/2,5-Xylenol | | 1.6 | 4.3 | 4.0 | 2.4 | 3.0 | 2.1 | 4.5 |
| 2,3-Xylenol | | Tr | 0.1 | 0.1 | Tr | 0.1 | Tr | Tr |
| 2,4,6-Trimethylphenol | | 2.7 | 3.2 | 2.2 | 1.5 | 1.6 | 1.0 | 3.1 |

*Regenerated catalyst

EXAMPLE 2

A sample of the improved catalyst of the present invention was prepared utilizing only 1% sodium silicate in place of the 3% sodium silicate plus 3% silica sol shown in the results generated in Table 1. The data of Table 3 is directly comparable to the data of Table 1 with this one difference. The results obtained from a catalyst containing only sodium silicate are shown in Table 3.

Table 3

| 1%SiO₃, WO/MgO Catalyst | | | | | |
|---|---|---|---|---|---|
| Hrs on Steam | | 4.0 | 28 | 72 | 80–96* |
| Temperature, °C | | 460 | 460 | 470 | 480 |
| Composition w/o | Feed | | | | |
| Water | 9.09 | | | | |
| Phenol | 43.0 | 32.2 | 34.0 | 34.9 | 33.4 |
| o-Cresol | .6 | 23.1 | 21.8 | 20.0 | 22.5 |
| m,p-Cresol | 5.1 | 7.3 | 5.7 | 4.5 | 4.5 |
| 2,6-Xylenol | 51.3 | 27.1 | 32.8 | 37.0 | 34.7 |
| 2,4/2,5-Xylenol | | 6.2 | 3.7 | 2.0 | 2.6 |
| 2,3-Xylenol | | .2 | .1 | .1 | .2 |
| 2,4,6-Trimethylphenol | | 2.9 | 2.0 | 1.4 | 1.5 |

*Composite

EXAMPLE 3

A catalyst of the instant invention as described and tested in Table 1 was tested for activity in olefin disproportionation.

The olefin used was 1-octene which was passed over the catalyst at 200° and 250° C at 0.33 liquid hourly space velocities in a continuous reactor. No ethylene or 7-tetradecene were observed in the products. The catalysts therefore did not disproportionate the olefin, although tungsten oxide and silica together with magnesium oxide is a catalyst for olefin disproportionation as taught in U.S. Pat. No. 3,786,112.

EXAMPLE 4

A reaction as described in Table 1 was carried out using as a catalyst only silica sol and sodium silicate. No reaction was observed to occur. It is therefore apparent that these materials acting along do not catalyze the instant reactions.

The catalyst of the instant invention is especially useful for the production of 3,5-xylenol as the major component in the disproportionation of tetramethylphenols and pentamethylphenols with phenol using the improved catalyst of the instant invention. It has been unexpectedly found that the 3,5-xylenol is by far the major component in the xylenol fraction and thus interference problems with closely boiling xylenols are avoided. Cresols and tri-substituted phenols also obtained as by-products can be easily separated by means well-known to those skilled in the art such as fractional distillation. Thus 3,5-xylenol can be obtained selectively in the disproportionation reaction without the incidental separation problems which have hitherto accomplished such a synthesis. This reaction is shown in Example 5.

EXAMPLE 5

Ortho and para methyl groups in highly methylated phenols were selectively removed in the presence of water and a catalyst comprised of 89% MgO, 3% $H_2WO_4$, 3% silica sol and 3% silica, all based on the total weight of the catalyst. Graphite (2%) was included as a lubricant. The reaction was carried out at a temperature of 470° C, with 9 weight percent water in the feed, and an LHSV of .25 in a continuous feed reactor. The products obtained from the reaction is shown in Table 4 wherein the feed and the products are compared.

Table 4

| DISPROPORTIONATION OF BOTTOMS WITH PHENOLS | | |
|---|---|---|
| Composition | Feed | Product |
| Phenol | 76.2 | 50.5 |
| o-Cresol | | 17.7 |
| m,p-Cresol[1] | | 10.4 |
| 2,6-Xylenol | | 1.4 |
| 2,4/2,5-Xylenol[2] | | 3.9 |
| 3,5-Xylenol | | 10.6 |
| 3,4-Xylenol | | 0.4 |
| 2,4,6-Trimethylphenol | | 0.1 |
| 2,3,6-Trimethylphenol | | 0.2 |
| 2,3,5/2,4,5-TMP | 0.9 | 2.5 |
| 2,3,4/3,4,5-TMP | 0.9 | 1.4 |
| PMB | 0.6 | 0.2 |
| 2,3,4,6/2,3,5,6-TeMP | 13.6 | 0.4 |
| 2,3,4,5-TeMP | 2.4 | 0.4 |
| HMB | 0.5 | Tr |
| Pentamethylphenol | 4.8 | Tr |

[1] 2/1 p/m ratio
[2] Mostly 2,4-Xylenol.

The reaction of phenol and 2,6-xylenol on the catalyst to yield o-cresol is promoted by the catalyst of this invention. Water in the reaction helps maintain high catalyst activity. The conversion is dependent on water concentration up to about 10 to 15 weight percent. Although the mechanism of the reaction is not known, it seems likely that hydrated MgO and hydrated $WO_3$ play an important part. If the catalyst is dried in regeneration, the initial activity is low and gradually increases with run time. Often 6-12 hours are required to reach maximum activity. This time to reach maximum activity can be reduced if water (steam) is used all through the regeneration procedure with air at 500° C, and it can be almost eliminated if start-up is conducted with steam only as the feed until reaction temperature is achieved.

The catalysts of this invention can function as mathylating catalysts if methanol is present. Ordinarily little or no free methanol is observed in the products of disproportionation. However, when methanol is added, the results are most different from MgO catalysts. The catalyst disclosed herein methylates at a lower methanol mole ratio and gives 2,4,6-TMP as the principal product at higher methanol mole ratios. A summary of the data obtained at a methanol/phenol mole ratio of 4/1 and 7.5/1 is given in Table 5. The product distribution of the 4/1 mole ratio reaction is important because of the high cresol content compared to the xylenol content in order to compare the product with known standards. The para content of this product was determined by silation. An equal volume of sample phenolics and hexamethyldisilazane with a catalytic amount of CATAPAL SB alumina was refluxed at 220° C for 24 hours to form the silyl ethers. No meta-cresol was observed in the silated product, and the only xylenol was 2,4-xylenol.

TABLE 5

| PHENOL METHYLATION | | | | | |
|---|---|---|---|---|---|
| Methanol/phenol Mole ratio | 4.0 | 4.0 | 7.5 | 7.5 | 7.5 |
| Temperature, ° C | 455 | 465 | 455 | 445 | 470 |
| LHSV | 0.5 | 0.5 | 0.5 | 0.5 | 0.5 |
| Composition (w/o) | | | | | |
| Anisole | 2.7 | 3.5 | 2.1 | 2.6 | 1.9 |
| Phenol | 64.5 | 35.8 | 14.8 | 45.1 | 11.7 |
| o-Methylanisole | 0.3 | 1.0 | 2.0 | 0.8 | 2.0 |
| o-Cresol | 20.4 | 31.0 | 16.7 | 24.2 | 13.3 |
| m,p-Cresol | 5.5 | 4.8 | 1.3 | 4.0 | 1.4 |
| 2,6-Xylenol | 2.2 | 9.8 | 26.3 | 12.5 | 27.8 |
| 2,4/2,5-Xylenol | 3.7 | 9.1 | 9.2 | 7.1 | 7.9 |
| 2,3-Xylenol | Tr | Tr | 0.6 | Tr | 0.9 |
| 2,4,6-Trimethylphenol | 0.7 | 5.0 | 27.0 | 3.8 | 32.7 |

Phenol methylation is carried out at temperatures of 400° to 500° C and an LHSV of about 0.1 to 10, although 0.5 to 5 is preferred. No pressures above atomspheric are necesary, although the reaction will proceed at higher pressures.

The role of phenol in the reactions involving disproportionation is both as a methyl group acceptor and as a diluent for 2,6-xylenol. It is important that there be nearly equal molar quantities of phenol and 2,6-xylenol in the feed because 2,6-xylenol will serve as a methyl group acceptor itself (Table 6) leading to a high 2,4,6-TMP level. Water added to feed is not necessary during methylation reactions, since water is formed during the reaction.

TABLE 6

| DISPROPORTIONATION OF 2,6-XYLENOL | | |
|---|---|---|
| Composition w/o | Feed | Product |
| Phenol | | 3.8 |
| o-Cresol | | 17.9 |
| m,p-Cresol | 4.1 | 4.9 |
| 2,6-Xylenol | 95.9 | 35.5 |
| 2,4/2,5-Xylenol | | 19.6 |
| 2,4,6-TMP | | 18.3 |

If the products of the reaction are recycled, there is a mechanism for removal of p-cresol but reaction involving meta positions is very slow.

Representative examples of phenols which can be disproportionated using the improved catalyst of the instant invention are 2,6-xylenol, 2,4-xylenol, 2,5-xylenol, 3,5-xylenol, 3,4-xylenol, 2,4,6-trimethylphenol, 2,3,6-trimethylphenol, 2,3,5-trimethylphenol, 2,4,5,-trimethylphenol, 2,3,4-trimethylphenol, 3,4,5-trimethylphenol, 2,3,4,6-tetramethylphenol, 2,3,5,6-tetramethylphenol, 2,3,4,5-tetramethylphenol and pentamethylphenol. It will be realized by those skilled in this art that any methyl group described above can be replaced by an alkyl group of from 2-10 carbon atoms. Other compound which can be disproportionated are pentamethylbenzene and hexamethylbenzene.

EXAMPLE 6

The catalyst described in Table 1 was used to disproportionate a bottoms product with phenol at 470° C. The bottoms had the following composition in weight percent based on the total:

| | |
|---|---|
| o-cresol | 0.52 |
| 2,6 xylenol | 7.24 |
| 2,4 xylenol | 8.66 |
| 3,4 xylenol | 2.78 |
| 2,4,6 trimethylphenol (TMP) | 79.00 |
| 2,3,6 TMP | 0.66 |
| other TMP | 0.88 |
| Tetra MP | 0.26 |

Water was added to the feed to equal 9.1 weight percent based on the total feed. A continuous reactor was used, and the LHSV was varied. The results are shown in Table 7.

TABLE 7

| FEED (calculated without H₂O) | LHSV | | |
|---|---|---|---|
| | 1.0 | 0.5 | 0.25 |
| Phenol 59.5 | 39.2 | 33.3 | 33.2 |
| o-cresol .2 | 19.3 | 27.0 | 27.4 |
| p-cresol - | 10.0 | 13.1 | 13.4 |
| 2,6 xylenol 3.0 | 5.6 | 6.3 | 6.4 |
| 2,4 xylenol 3.7 | 13.9 | 14.4 | 14.0 |
| 3,4 xylenol 1.2 | 0.6 | 0.4 | 0.3 |
| 2,4,6 TMP 31:4 | 10.4 | 5.1 | 5.1 |
| 2,3,6 TMP 0.4 | 0.1 | 0.1 | 0.1 |
| higher TMP 0.6 | 0.4 | 0.2 | 0.3 |

EXAMPLE 7

Mixtures of xylenols and 2,4,6-trimethylphenol were disproportionated with phenol at 40° C and 0.5 LHSV using the catalyst of Table 1. Water was present at 9.1 weight percent. The results are shown in Table 8.

TABLE 8

| FEED | | PRODUCT |
|---|---|---|
| Phenol | 60.72 | 42.7 |
| o-cresol | — | 21.5 |
| m,p-cresol | — | 17.0 |
| 2,6 xylenol | 2.4 | 2.4 |
| 2,4/2,5 xylenol | 18.9 | 10.3 |
| 2,3 xylenol | 8.5 | 2.2 |
| 3,4 xylenol | — | 0.7 |
| 2,4,6 TMP | 7.0 | 1.2 |
| 2,3,6 TMP | 1.3 | 0.6 |
| higher TMP | 1.2 | 1.3 |

Through this specification and claims the terminology m,p-Cresol is used to indicate a mixture of meta and para cresols, and references to MgO/WO₃ catalyst relate to the catalysts of the instant invention which also include silica sol and silica unless otherwise stated.

While certain embodiments and details have been shown for the purpose of illustrating this invention, it will be apparent to those skilled in this art that various changes and modifications may be made herein without departing from the spirit or the scope of the invention.

I claim:

1. In a process for the disproportionation of xylenols, trialkyl phenols, tetra-alkyl phenols, and pentaalkyl phenols and mixtures of these with phenol, wherein the alkyl groups of each contain from 1 to 10 carbon atoms, to form cresols and xylenols by contacting said alkylated phenols with phenol in the presence of a catalyst of magnesium oxide, promoted with from about 0.5 to about 15 weight percent tungsten oxide based on the total catalyst weight, in vapor phase at temperatures of from about 350° to about 550° C and pressures of up to about 1,000 pounds per square inch gauge (psig), the improvement comprising synergistically increasing catalytic activity with sodium silicate and silica sol while adding from about 1 to about 15 weight percent water to the feestream based on the total weight of the feed, and carrying out the reaction at a liquid hourly space velocity (LHSV) of from 0.5 to about 5 in a continuous flow reactor.

2. A method as described in claim 1 wherein the alkylated phenols are tetramethylphenols and pentamethylphenols and 3,5-Xylenol is the major product component.

3. A method as described in claim 1 wherein sodium silicate is present from about 1 to about 5% by weight and silica sol is present from about 1 to about 5% by weight, based on the total catalyst weight.

4. A method as described in claim 1, wherein the phenol is 2,6-xylenol and the major product is o-cresol.

5. A process as described in claim 1 wherein the phenol is essentially 2,4,6-trimethylphenol and the primary products are ortho cresol and para cresol.

6. In a process for the methylation of phenol by contacting phenol with methanol in the presence of a catalyst comprising magnesium oxide promoted with from about 0.5 to about 15 weight percent tungsten oxide based on total catalyst weight in vapor phase at temperatures of from about 400° to about 500° C, the improvement comprising synergistically increasing catalyst activity with from about 1 to about 5 weight percent each of sodium silicate and silica sol and carrying out the reaction in a continuous flow reactor at an LHSV of from 0.5 to about 10.0.

* * * * *

UNITED STATES PATENT OFFICE
CERTIFICATE OF CORRECTION

PATENT NO. : 4,125,736
DATED : November 14, 1978
INVENTOR(S) : Bruce E. Leach

It is certified that error appears in the above-identified patent and that said Letters Patent are hereby corrected as shown below:

Column 2, line 59, "45°" should be --450°--.

Column 3, Table 1, in the heading, "$NaSiO_3$" should be --$Na_2SiO_3$--.

Signed and Sealed this

Fifteenth Day of May 1979

[SEAL]

Attest:

RUTH C. MASON
Attesting Officer

DONALD W. BANNER
Commissioner of Patents and Trademarks